United States Patent
Scott et al.

(10) Patent No.: US 9,938,201 B1
(45) Date of Patent: Apr. 10, 2018

(54) MICRONUTRIENT COMPOSITIONS CONTAINING ZINC AND SYSTEMS AND METHODS OF USING SAME

(71) Applicant: Winfield Solutions, LLC, Shoreview, MN (US)

(72) Inventors: James Dwight Scott, Anacortes, WA (US); Danny Brown, Woodbury, MN (US)

(73) Assignee: WINFIELD SOLUTIONS, LLC, Shoreview, MN (US)

( * ) Notice: Subject to any disclaimer, the term of this patent is extended or adjusted under 35 U.S.C. 154(b) by 32 days.

(21) Appl. No.: 15/053,711

(22) Filed: Feb. 25, 2016

(51) Int. Cl.
  *C05F 11/10* (2006.01)
  *C05D 9/02* (2006.01)
  *C05G 3/02* (2006.01)
  *A01N 57/20* (2006.01)

(52) U.S. Cl.
  CPC .............. *C05D 9/02* (2013.01); *A01N 57/20* (2013.01); *C05F 11/10* (2013.01); *C05G 3/02* (2013.01)

(58) Field of Classification Search
  CPC ....................................... C05F 11/10
  USPC ....................................... 504/126
  See application file for complete search history.

(56) References Cited

U.S. PATENT DOCUMENTS

| | | | |
|---|---|---|---|
| 2,960,406 A * | 11/1960 | Cardon | A23K 20/30 426/2 |
| 3,493,557 A | 2/1970 | Ramsden | |
| 5,504,055 A | 4/1996 | Hsu | |
| 5,997,600 A | 12/1999 | Dean | |
| 6,197,815 B1 | 3/2001 | Hsu | |
| 7,666,242 B2 | 2/2010 | Gednaslke et al. | |
| 8,685,133 B2 | 4/2014 | Ponder et al. | |
| 2005/0239673 A1 | 10/2005 | Hsu | |
| 2010/0273656 A1 | 10/2010 | Sedun et al. | |
| 2015/0250165 A1* | 9/2015 | Balastre | A01N 25/04 106/162.8 |

FOREIGN PATENT DOCUMENTS

WO  WO 1993022919  11/1993

OTHER PUBLICATIONS

Max-In® Zinc Label, Winfield, 3 pages, Nov. 2, 2015.
Max-In® Zinc Pamphlet, Winfield, 2 pages, 2015.
Max-In® Zinc Safety Data Sheet, Winfield, 5 pages, Mar. 20, 2015.
Weed Control Alert, Guidelines for Use With AMS, Roundup PROMAX®, 2 pages, downloaded Feb. 2016, http://www.monsantoito.com/docs/PROMAX_Amonium_Sulfate_use_Hard_Water_issue_TUG.pdf.
Wyrill, J.B. III et al., "Glyphosate Toxicity to Common Milkweed and Hemp Dogbane as Influenced by Surfactants", Weed Science, vol. 25, No. 3 (May, 1977), pp. 275-287.
Roundup Weathermax MSDS, [online] (May 3, 2016), obtained from the URL <http://roundup.ca/_uploads/documents/Roundup%20WeatherMAX-Label_EN_04 1 6_pdf>.

* cited by examiner

*Primary Examiner* — Johann R Richter
(74) *Attorney, Agent, or Firm* — Dorsey & Whitney LLP; Bridget M. Hayden

(57) ABSTRACT

A chelated zinc adjuvant composition includes water, an effective amount of a micronutrient consisting of zinc chelated with an organic acid and an organic amine, a mono-, di- or polysaccharide and an alkyl polysaccharide. The adjuvant has a pH of up to 6.5. When admixed with a pesticide capable of precipitating with the zinc, due to the zinc being chelated, the zinc is prevented from precipitating with the pesticide and is available for uptake. When the adjuvant composition is applied in seed, soil, foliage or fruit applications, zinc uptake is improved.

14 Claims, 1 Drawing Sheet

MICRONUTRIENT COMPOSITIONS CONTAINING ZINC AND SYSTEMS AND METHODS OF USING SAME

TECHNICAL FIELD

The present disclosure relates to products, systems and methods of using micronutrient compositions in seed, soil, foliar and fruit applications, and more particularly to improving the availability of zinc for plant uptake in such applications.

BACKGROUND

Crop protection involves application of herbicides, insecticides, fungicides, collectively known as pesticides, to control the growth of weeds, harmful insects and plant diseases that afflict crops. Without these practices, food production would decline, many fruits and vegetables would be in short supply, and the price of food would rise. Further, fibers for textile manufacturing, such as cotton, would decrease as farmers would lose their harvests due to pests and diseases.

Pesticides are typically applied in combination with adjuvants to improve pesticide performance. Adjuvants are substances in a pesticide formulation or added to the spray tank to improve pesticidal activity or application characteristics. In addition, micronutrients may be applied in combination with pesticides and adjuvants. Micronutrients includes elements essential for plant growth and include boron (B), copper (Cu), iron (Fe), chloride (CI), manganese (Mn), molybdenum (Mo) and zinc (Zn). For instance, boron assists plants in use and regulation of other nutrients, aids production of sugar and carbohydrates, and is required for seed and fruit development. Copper is important for reproductive growth, aids in root metabolism and helps in the utilization of proteins. Chloride aids plant metabolism. Iron is a necessary micronutrient in the formation of chlorophyll. Manganese is used by plant enzyme systems and is involved in the breakdown of carbohydrates, as well as nitrogen metabolism. Molybdenum assists in the use of nitrogen. Zinc is needed by the plant for regulating plant growth and in carbohydrate and sugar metabolism. While some micronutrients are found in soil, others are not; and some soil-based micronutrients may not be at levels sufficient for plant growth.

However, many pesticides contain phosphate salts that bind to the metal ions of the micronutrient and convert them to insoluble solids before the micronutrient can be absorbed by the plant, rendering micronutrient ineffective. In prior approaches, ethylenediaminetetraacetic acid (EDTA) has been used as a chelating compound that operates to bind metal ions of the micronutrient and prevents phosphate salt from converting the micronutrients to insoluble solids. While EDTA prevents phosphate from binding to metal ions, the metal ions exhibit diminished reactivity and the EDTA can cause phytotoxicity. In addition, EDTA is not accepted for use as a chelator in all countries. Other chelating compounds include organic acids and amino acids such as those described in U.S. Pat. No. 5,504,055 and US Patent Application Publication 2005/239673, which are incorporated herein for any purpose.

SUMMARY

In view of the foregoing, implementations provide an adjuvant composition that includes water; an organic acid; an organic amine; a mono-, di- or polysaccharide; an alkyl polysaccharide; and an effective amount of a micronutrient consisting of zinc. A pH of the adjuvant is up to 6.5.

In some variations and alternatives, the pH of the adjuvant is from about 2.0; the zinc may be present at about 1 to about 10 wt % of the composition, and in addition, the zinc may be chelated with an organic acid and the organic amine; the mono-, di- or polysaccharide may be fructose; and/or the alkyl polysaccharide may be an alkyl polyglycoside non-ionic surfactant.

According to further implementations, a method of providing an agricultural admixture involves admixing an adjuvant composition with a pesticide in which the adjuvant composition includes water; an organic acid; an organic amine; a mono-, di- or polysaccharide; an alkyl polyglycoside non-ionic surfactant; and an effective amount of a micronutrient consisting of zinc. In such implementations, the pesticide may be at least one component capable of precipitating with the zinc, the zinc may be chelated with the organic acid and the organic amine, thereby preventing the zinc from precipitating with the pesticide, and a pH of the admixture may be up to about 6.5.

In some variations and alternatives, the pesticide includes glyphosate, and in such an approach, the method may involve admixing with hard water; the adjuvant composition and the pesticide may be free of other micronutrients; the zinc may be present at about 1 to about 10 wt % of the composition; and/or the adjuvant may be buffered to retain the pH of the admixture below about 6.5.

Is yet further implementations, a method of improving uptake of zinc in seed, soil, foliar and fruit applications involves applying to the seed, soil, foliage or fruit, an adjuvant composition including an organic acid; an organic amine; a mono-, di- or polysaccharide; an alkyl polysaccharide; and an effective amount of a micronutrient consisting of zinc. In response, the seed, soil, foliage or fruit increases uptake of the zinc.

In some variations and alternatives, a pH of the applied adjuvant composition is up to about 6.5; the method may further involve admixing the adjuvant composition with a pesticide prior to foliar application, in such approaches, the pesticide may be glyphosate, and in addition or alternatively, the adjuvant composition and the pesticide may be free of other micronutrients; zinc may be present in the composition as zinc oxide at about 1 to about 10 wt % of the composition; the mono-, di- or polysaccharide may be fructose; and/or the alkyl polysaccharide may be an alkyl polyglycoside non-ionic surfactant.

In other implementations, provided herein are compositions containing a mixture of zinc and one or more agricultural chemicals that are otherwise capable of precipitating with zinc (e.g., zinc oxide), and approaches for using these compositions.

Other features and advantages of the present disclosure will become more fully apparent and understood with reference to the following description and accompanying drawings and claims.

BRIEF DESCRIPTION OF THE DRAWINGS

FIG. 1 is a chart illustrating the results of tissue testing of corn, wheat and cotton in zinc deficient plants after treatment with the adjuvant composition containing zinc, according to the present disclosure.

DETAILED DESCRIPTION

Implementations provide micronutrient compositions containing zinc that can be used in agricultural applications where plants or soil have a zinc deficiency. The compositions may be provided as an adjuvant, which may include components both for chelating the zinc, making the zinc available for uptake, as well as for delivering the zinc to leaves, seeds or soil. The composition may be applied to a broad spectrum of crops in order to enhance leaf and vascular growth and root development.

As an adjuvant composition, the micronutrient compositions containing zinc may include but are not limited to: water; an organic amine; an organic acid; a mono-, di-, and polysaccharide; and an alkyl polysaccharide. The adjuvant composition may have a pH that is below 6.5 or ranges from 2.0 to 6.5. Glyphosate or other pesticides may be compatible with the adjuvant composition and may be admixed prior to application.

Water may be present in the adjuvant at about 40 to about 60 wt %, about 45 to about 60 wt %, about 50 to about 60 wt %, or about 50 to about 55 wt % of the adjuvant composition.

Organic amines present in the adjuvant composition may include but are not limited difunctional and multi-functional amines such as monoethanolamine (MEA), dimethylaminopropylamine, diethylamine (DEA), dimethylamine (DMA), triethylamine (TEA), and diethylenetriamine (DETA). The organic amine may be present in a range from about 1 to about 12.5 wt %, about 5 to about 12.5 wt %, about 8 to about 12.5 wt %, about 9 to about 12.5 wt %, about 10.5 to about 12.5 wt %, or at about 11.5 wt % of the adjuvant composition.

Organic acids may include but are not limited to: citric acid, gluconic acid, lactic acid, malonic acid, tartaric acid, glutamic acid, fumaric acid, oleic acid, acetic acid, glutaric acid, malic acid, ascorbic acid, or combinations thereof. The organic acid may be present in a range from about 10 to about 25 wt %, about 10 to about 20 wt %, about 15 to about 20 wt %, about 15 to about 25 wt %, or about 18 to about 23 wt % of the adjuvant composition. At such ranges, the organic acid may be present in the composition at a sufficient level to maintain the pH at or below 6.5.

Micronutrients present in the adjuvant composition may include zinc. The micronutrient may be present at about 1 to about 10 wt %, about 3 to about 9 wt %, about 4 to about 8 wt %, about 4 to about 7 wt %, about 5 to about 7 wt %, or at about 6 wt % of the adjuvant composition. In a particular example, zinc may be provided in the form of zinc oxide (ZnO) and may be present in a range from about 1 to about 10 wt %, about 3 to about 9 wt %, about 4 to about 8 wt %, about 6 to about 8 wt %, about 6 to about 10 wt %, or at about 7.5 wt % of the adjuvant composition. Zinc may also be provided as zinc carbonate ($ZnCO_3$) and may be present in a range from about 1 to about 15 wt %, about 5 to about 15 wt %, about 8 to about 15 wt %, about 8 to about 13 wt % or about 12 wt % of the adjuvant composition. Other micronutrients may be provided alone or in combination with zinc include boron (B), copper (Cu), iron (Fe), chloride (CI), manganese (Mn), molybdenum (Mo), magnesium (Mg), calcium (Ca) and cobalt (Co).

According to certain implementations, aside from zinc, the adjuvant may otherwise be free of other micronutrients, such as micronutrients containing boron (B), copper (Cu), iron (Fe), chloride (CI), manganese (Mn), molybdenum (Mo), magnesium (Mg), calcium (Ca) and cobalt (Co). For instance, the adjuvants and other compositions of the present disclosure may consist exclusively of the specifically recited micronutrients. The recited compositions may contain various impurities, but in such amounts so as not to effect the advantageous properties of the inventive compositions that promote the uptake of zinc. Preferably, such trace amounts of material will be present in less than 1000 ppm.

Zinc in the adjuvant composition may be bound (e.g., chelated) with the organic amine and the organic acid in order to prevent salts (e.g. phosphate salts) commonly found in agricultural chemicals from converting zinc ions to an unusable, insoluble solid. The compositions, accordingly, may provide compatibility for micronutrients admixed with pesticides. Chelation of zinc may further prevent fouling of spray equipment.

According to certain implementations, a molar ratio of the zinc:organic amine:organic acid may be 1:2:1. For instance 1 mole of zinc may be provided for every two moles of MEA and every 1 mole of citric acid. In this example, the citric acid being a diprotic acid with two carboxylic groups requires 2 moles of the amine groups in the MEA to enable the carboxylic functional groups on the citric acid to chelate with the zinc. The chelated adjuvant compositions appear clear in solution.

Mono-, di-, and polysaccharides may include but are not limited to: glucose, fructose, galactose, mannose, lactose, fucose, xylose, amylose, raffinose, maltotriose, glucosides, trehalose; saccharide alcohols such as mannitol, sorbitol, xylitol and maltitol; compositions containing sugar such as molasses; and combinations and variations thereof. The mono-, di-, and polysaccharides may be present in a range from about 1 to about 20 wt %, about 1 to about 15 wt %, about 1 to about 10 wt %, about 1 to about 7.5 wt %, or about 1 to about 5.0 wt % of the adjuvant composition.

The alkyl polysaccharide of the present invention may be a commercially available surfactant. The alkyl polysaccharides may be present in a range from about 1 to about 20 wt %, about 1 to about 15 wt %, about 1 to about 10 wt %, about 1 to about 7.5 wt %, about 1 to about 5.0 wt %, or about 1 to about 3.5 wt % of the adjuvant composition. Alkyl polysaccharides may include but are not limited to: Agrimul PG 2069®, available from Henkel Corporation of Ambler, Pa.; APG 325®, available from BASF Corporation of Florham Park, N.J.; and AT Plus 438®, available from Uniqema Surfactant of Wilmington, Del.; APG 911 and APG 810, available from Adjuvants Unlimited. Agrimul PG 2069® is an alkyl polyglycoside non-ionic surfactant and includes alkyl polyglycoside polymers with alkyl chains of nine carbons in a concentration of 20% by weight, ten carbon atoms in a concentration of 40 wt % and eleven carbon atoms in a concentration of 40% wt %. The alkyl polyglycoside has an average degree of polymerization of 1.6, and is considered a non-ionic surfactant. It is non-gelling, biodegradable and soluble in dispersions of high salt concentrations. AT Plus 438 is an alkyl polysaccharide based on glucose and fatty alcohols derived from plant sources.

Inert components, such as surfactant additives, may include but are not limited to: isopropyl alcohol (IPA), propylene glycol (PG), and a poly-siloxane foam retardant (Si). These inert components may be nonfunctioning agents or formulation aids, e.g., for reducing the freezing temperature. The inert components may be present in a range from about 0.1 to about 5 wt %, about 0.1 to about 3 wt %, about 1 to about 3 wt %, about 1 to about 2 wt %, or about 2 wt % of the adjuvant composition. Other inert components include anti-foaming agents or defoamers, which may be present in the composition and may include but are not limited to silicone-based defoamers. These components may be present in a range from about 0.01 to about 0.5 wt %, or about 0.1 wt % of the adjuvant composition. Antimicrobials, another inert component, may be present in the composition and may include but are not limited to 1,2-benzisothiazolin- 3-one in dipropylene glycol—antimicrobial (e.g., Proxel™ GXL, available from Arch Biocides of Smyrna, Ga.). These components may be present in a range from about 0.01 to about 0.1 wt %, or up to about 0.1 wt % of the adjuvant composition.

FIG. 1 is a chart illustrating the results of tissue testing of corn, wheat and cotton in zinc deficient plants after treatment with the zinc-containing adjuvant composition of the present disclosure. As illustrated, about 80 percent of corn plants, about 75 percent of wheat plants, and about 50 percent of cotton plants tested showed a response to the zinc treatment. In the compositions of the present disclosure, the chelated zinc is more readily available for uptake by the plant, and the mono-, di-, and polysaccharides along with the alkyl polysaccharide may increase droplet spread, leaf coverage and humectancy, and therefore may enhance movement of zinc and other nutrients through the plant via leaf cuticle to internal leaf structures and/or into the seed for improved vascular growth and root development. By introducing zinc to the plant, a more robust root system is developed, which improves nutrient uptake and makes water use more efficient. The zinc may help reduce the impact of heat stress, drought stress, and further, may improve yield.

The adjuvant composition of the present disclosure has a pH that ranges from 2.0 to 6.5, 3.0 to 6.5, 4.0 to 6.5, at or about 5.0 to 6.5, about 5.0 to about 6.0, about 5.5 to 6.5, about 6.0 to 6.5, or up to 6.5. These ranges provide an acidic or a slightly acidic pH to the adjuvant composition. The organic acid, e.g., citric acid, provides acidity to the adjuvant, while simultaneously chelating with the zinc in the adjuvant composition. The acidic adjuvant compositions of the present disclosure are in contrast to the fertilizer compositions taught by U.S. Pat. No. 5,997,600 that are maintained at a pH above 7.5. In some implementations, the organic acid may be present in excess to maintain the acidity of an agricultural admixture when alkaline components, such as hard water having a pH greater than 7 is used in the admixture. In additional or alternative implementations, the organic acid may buffer the adjuvant composition. For instance, a mixture of an organic acid and its sodium salt may provide a buffering solution. In a more particular example, a mixture of citric acid and sodium citrate may provide a citrate buffer. In another example, a mixture of citric acid and disodium phosphate may provide a phosphate-citrate buffer.

According to the present disclosure, the organic amine, e.g., monoethanolamine may be provided in a quantity sufficient to chelate with the zinc, however, the organic amine may not be provided in great excess, e.g., a maximum of 12.5 wt % of the adjuvant composition. More particularly, it has been discovered that an excess of the organic acid or the buffered organic acid sufficient for both chelation and maintaining the pH in the slightly acidic to acidic range, along with an amount of organic amine sufficient for chelation, provides an adjuvant composition advantageous for use in combination with pesticides containing glyphosate. Glyphosate is a herbicide commonly used to control weeds in glyphosate-resistant crops. Glyphosate being a weak acid has a limited ability to counteract the effects of alkaline solutions, e.g., hard water, and can dissociate under these conditions, rendering the glyphosate ineffective. According to the present disclosure, the adjuvant composition, glyphosate, and hard water or another alkaline solution may be admixed and sprayed simultaneously. The buffering ability of the adjuvant composition in the acidic range provides the admixture with a pH of up to about 6.5, preferably in the range of 5 to 6, and enables the delivery of the chelated zinc to soil, seeds, foliage or fruit along with the effective application of the glyphosate for the simultaneous control of weeds.

A number of pesticides, e.g., herbicides, insecticides and/or fungicides are compatible with the adjuvant compositions of the present disclosure. Some preferred herbicides include but are not limited to glyphosate (e.g., N-(phosphonomethyl)glycine) in various forms including in the form of a salt, ester or other derivative thereof. Examples of glyphosate products include but are not limited to: its form as a potassium salt (e.g., Roundup PowerMax® and Touchdown Total®), as a dimethylamine salt (e.g., Durango® DMA®), in is form as an isopropylamine salt (e.g., Cornerstone® 5 plus), and glyphosate in combination with other pesticides such as 2,4-Dichlorophenoxyacetic acid (2,4-D) (e.g., Enlist Duo™) and with dicamba (e.g., Mon 76832 and Roundup® Xtend).

Other compatible herbicides include, but are not limited to: the sodium salt of bentazon (3-(1-methylethyl)-1H-2,1,3-benzothiadiazin-4 (3H)-one 2,2,-dioxide) (e.g., Basagran®); diglycolamine salt of 3,6-dichloro-o-anisic acid (e.g., Sterling® Blue); 3,6-dichloro-2-methoxybenzoic acid (e.g., Dicamba, Enginia™); 2,4-Dichlorophenoxyacetic acid (2,4-D); 1-chloro-3-ethylamino-5-isopropylamino-2,4,6-triazine (Atrazine); amide herbicides; arsenical herbicides; carbamate and tiocarbamate herbicides; carboxylic acid herbicides; dinitronailine herbicides; heterocyclic nitrogen-containing herbicides; organophosphate compounds; urea herbicides; and quaternary herbicides; 5-[2-chloro-4-(trifluoromethyl)phenoxy]-N-(methylsulfonyl)-2-nitrobenzamide (Fomesafen); tembotrione (e.g., Laudis®).

Types of weeds that may be controlled using the herbicide compositions may include, but are not limited to: barnyard grass, green foxtail, wild oats, nightshade, velvetleaf, annual morningglory, yellow nutsedge, pigweed, downy brome.

In addition or alternatively, the herbicides may include insecticides and/or fungicides. Insecticides that may be compatible with the disclosed compositions include but are not limited to: pyrethroid insecticides (e.g., bifenthrin); pyrethrins or other botanicals (e.g. D-limonene, linalool, ryania, rotenone, eugenol (clove oil); chloronicotinyls; essential oils (e.g., lemongrass, pepper wintergreen, rosemary, cinnamon, sesame, thyme, cedar oils and capsaicin); neem oil (e.g., Azadirachtin); nicotine; microbial products (e.g., *Bacillus thuringeinis* and *Beauveria bassiana*); oxadiazines (e.g., Indoxacarb); anthranilic diamide (e.g., chlorantraniliprole); juvenile hormone mimics (e.g., fenoxycarb; pyriproxifen; methoprene; and hydroprene), pyrroles (e.g., chlorfenapyr), phenylpyrazoles (e.g., fipronil), organophosphates (e.g., malathion and chlorpyrifos), inorganics (e.g., sulfur and dormant and horticultural oils); insect growth regulators such as chitin synthesis inhibitors (e.g., hexaflumuron; noviflumuron; diflubenzuron; buprofezine; cyromazine; and halofenozide); acaricides such as miticides (e.g., avermectin) and ixodicides alone or in any combination with the compositions of the present disclosure. Fungicides that may be compatible with the disclosed compositions include but are not limited to: fluxapyroxad, pyraclostrobin, propiconazole, trifloxystrobin, prothioconazole, 1,2-propanediol, azoxystrobin (e.g. Priaxor®, Onset®, Topaz®, Headline® amp, Headline® sc, Stratego®, Quadris®) alone or in any combination with the compositions of the present disclosure.

Other compatible pesticide additives may include nematocides, plant growth regulators and animal repellents.

When the water in an admixture containing herbicide is hard water, water conditioners such as Class Act® NG® may be admixed in order to prevent trace impurities from binding with the herbicide (e.g., precipitating). The water conditioner includes cations and anions that bind with the impurities making them unavailable for precipitating with the herbicide, and further, the water conditioner may bind to sites on the herbicide to further prevent the impurities from antagonizing the herbicide.

The adjuvants and other compositions of the present disclosure may consist exclusively of the specifically recited components. In addition or alternatively, the compositions may be free of certain components. For instance, an adjuvant-containing admixture of the present disclosure may be free of NPK fertilizers and chelators such as EDTA, fertilizers containing any of nitrogen, phosphorous or potassium, or free of any of the pesticides described. The recited compositions may contain various impurities, but in such amounts so as not to effect the advantageous properties of the inventive compositions that promote the uptake of zinc.

Uses

The adjuvant compositions may be applied in agricultural spray applications such as to seed, soil, foliage and fruit. Sprays containing the disclosed adjuvant compositions may be delivered using ground and aerial spray applications. Application may be during the vegetative state and may range from v3 to v18. In addition or alternatively, the adjuvant may be applied during or after planting to promote the growth of the plant root system.

Prior to use, the disclosed compositions may be mixed with, for instance, water, water conditioners, pesticides, antimicrobial compositions, and inert components described herein such as formulation aids (e.g., propylene glycol) and surfactants (e.g., cationic, anionic and/or nonionic surfactants). Admixing may be conducted under agitation. In addition or alternatively, admixing may take place at ambient temperatures, e.g., about 70 to 90° F. depending on climate, or may take place under elevated temperatures above 90° F. Admixtures containing the adjuvant composition and a herbicide may have a pH below 6.5, and preferably in the pH range of about 5 to about 6.

Uptake of the chelated zinc present in the adjuvant compositions by seed, soil, foliage and fruit may facilitate improving growth of plants that are zinc deficient, and zinc uptake may be improved compared to prior approaches in which unchelated zinc is applied. For instance, when applied to growing plants, the plants readily uptake the chelated zinc when applied at rates of 32 oz. and 64 oz. per acre. In addition, the adjuvant compositions of the present disclosure are compatible with herbicides such that when admixed with a herbicide and applied to herbicide-resistant plants, the plants readily uptake the chelated zinc while enabling the herbicide to simultaneously control weeds. Particularly the chelated zinc does not antagonize herbicides, when enables producers to make fewer spraying passes in fields. As compared to an application of unchelated zinc, the uptake of chelated zinc is relatively improved. Further, the adjuvant compositions of the present disclosure are compatible with herbicides, which enables the adjuvant compositions to be safely admixed with herbicides while avoiding precipitation of the herbicide and zinc, which could otherwise clog spray equipment, e.g., spray nozzles. Improved uptake of the chelated zinc adjuvant compositions as well as the compatibility of the adjuvant compositions are discussed further in the Examples. Those of skill will understand that the following Examples are provided for purposes of illustration and should not be construed as limiting.

EXAMPLES

Uptake/Efficiency

Study 1:

A zinc foliar uptake trial using the zinc-containing adjuvant composition and admixtures were conducted on corn in Florida during the 2015 growing season.

Materials and Methods:

In this study, four chelated zinc treatments were studied against a control. The control was untreated corn. The first treatment received 32 fluid oz. per acre of the zinc-containing adjuvant composition of the present disclosure including 6.0 wt % zinc chelated with MEA and citric acid admixed with high fructose corn syrup, and an alkyl polyglycoside non-ionic surfactant. This treatment also included glyphosate (RoundUp PowerMax (22 fluid oz. per acre)) and a water conditioner (Class Act NG (1%)). The second treatment received 64 fluid oz. per acre of the zinc-containing adjuvant composition and the same level of glyphosate and water conditioner as in treatment 1. The third treatment received 32 fluid oz. per acre of the zinc-containing adjuvant composition. The fourth treatment received 64 fluid oz. per acre of the zinc-containing adjuvant composition.

The trials were laid out on a randomized-complete block design with four replications. Plot size was 10 feet by 30 feet. Prior to the foliar application of the zinc-containing products, a composite tissue sample, comprised of the uppermost, fully developed corn leaf, was collected from across the trial area. This sample established the pre-existing zinc content of the corn plants.

Zinc uptake from a foliar application of the disclosed composition applied to corn at the V4-V5 growth stage and was measured by plant tissue analysis of the whole plant. A plant tissue sample was collected from each plot six days post-application. The sample was the uppermost, fully developed corn leaf taken from every plant from the center two rows of the plot. The center two rows were the only rows utilized to ensure the plants sampled received even coverage during product application and to eliminate the potential for spray-overlap. The corn tissue was analyzed by Midwest Laboratories (13611 B Street, Omaha, Nebr. 68144).

Results:

The average tissue level of zinc for the untreated control was 3 ppm, for the first treatment group was 44.75 ppm, for the second treatment group was 78.75 ppm, for the third treatment group was 26 ppm, and for the fourth treatment group was 43 ppm.

The results show improved zinc uptake for all treatments compared to the control, and as levels of chelated zinc in the adjuvant mixture increase, zinc uptake is increased. When admixed with glyphosate and a water conditioner, zinc uptake was further improved. However, weed control for the 32 oz./acre zinc treatment with glyphosate (treatment 1) killed 64% of weeds, which is an increase over the 64 oz./acre zinc treatment with glyphosate (treatment 2) in which 41% of weeds were killed. Consequently, the application rate of the zinc-containing adjuvant at the 32 oz./acre application rate does not antagonize the effectiveness of glyphosate and may be preferred when used in combination with other agricultural chemicals purposes of both zinc uptake and weed control.

Study 2:

A zinc foliar uptake trial was conducted on corn in Florida during the 2015 growing season.

In this study, two chelated zinc treatments were studied against a control containing no zinc, and a control containing unchelated zinc. The first treatment received 32 fluid oz. per acre of the zinc-containing adjuvant composition of the present disclosure. The second treatment received 64 fluid oz. per acre of the zinc-containing adjuvant composition. The control containing unchelated zinc was applied at 32 fluid oz. per acre.

The trial methods followed the same approach as study 1 except that the applications were applied at the V5 stage and only the top leaf was sampled.

Results:

The average tissue level of zinc for the untreated control was 2.3 ppm, for the first treatment group was 136.8 ppm, for the second treatment group was 237.8 ppm, and for the unchelated zinc control was 59.3 ppm.

The results show improved zinc uptake for all treatments compared to the control containing no zinc, and as levels of chelated zinc in the adjuvant mixture increase, zinc uptake is increased. Chelated zinc at the 32 oz. per acre application rate was significantly improved over the same application rate for the unchelated zinc.

Compatibility

The zinc-containing adjuvant compositions of the present disclosure were tested for compatibility with pesticides using a modified approach from ASTM E1518—05(2012), Standard Practice for Evaluation of Physical Compatibility of Pesticides in Aqueous Tank Mixtures by the Dynamic Shaker Method, ASTM International, West Conshohocken, Pa., 2012. The pesticides tested included: glyphosate including in its various forms including Roundup® PowerMax®, Durango®, Cornerstone® 5 plus, Touchdown Total®, Enlist Duo™ (containing glyphosate and 2,4-D) and MON 76382; 2,4-D; Sterling® Blue; Basagran®; Enginia™.

Materials and Methods:

The apparatuses used in compatibility testing included: 1. a graduated cylinder, 120 mL; 2. transfer pipets; 3. balance, ±0.01 g; 4. a sieve, U.S. standard, 50 mesh (300 µm), 3 inches in diameter; and 5. a flashlight. With respect to the reagents used, reagent grade chemicals were used in all tests and the water had a purity level of Type IV. Synthetic water was made according to CIPAC handbook F section MT18.

The final disposition of the compatibility test was on or around 100 mL, and the ratios needed to bring an application of 10 gallons per acre to 100 mL per acre were calculated. 70 percent of the water needed for the compatibility test was added to the cylinder at room temperature. The remaining components were added for the jar test according to WALES and DALES unless otherwise specified by the product label. Applications rates were used from the product label. The liquid products were delivered using the transfer pipet or weigh in solid products. After each individual product had been added, the jar was capped and swirled by hand until the product became homogenous. After all of the product water had been added, the remaining the water was be added. The entire mix was agitated for a period of no less than 30 seconds.

Testing and evaluations were conducted 0.25, 2, 6, 24, and 72 hours after agitating the mixture. Evaluations were separated into seven categories that are flocculation, sludge, gelling, clumping, precipitation, separation, and non-dispersible oil. A grading of 1-5 was used for each category (1 being the presence of none, 5 having the highest presence).

Results:

The results of the compatibility testing showed the admixtures of the zinc-containing adjuvant and the pesticides did not have any flocculation, sludge, gelling, clumping, precipitation, separation, or non-dispersible oil after 24 hours. All categories for each of the herbicides tested scored a 1 over this time period.

After 72 hours, the following pesticides had the same results as the 24 hour testing: Roundup® PowerMax®, Durango®, Touchdown Total®, Enlist Duo™ (containing glyphosate and 2,4-D) and MON 76382; 2,4-D; Sterling® Blue; Basagran®. For Cornerstone® 5 plus Enginia™, these herbicides contained some particles, but not at a level sufficient to block the mesh screen.

These results show that the zinc-containing adjuvant is compatible across a variety of herbicides, including herbicides containing various glyphosate salts.

While the present disclosure has been particularly shown and described with reference to embodiments thereof, it will be understood by those skilled in the art that various other changes in the form and details may be made without departing from the spirit and scope of the disclosure.

What is claimed is:

1. A method of providing an agricultural admixture for improving uptake of zinc in seed, soil, foliar, and fruit applications, the method comprising:
    admixing an adjuvant composition with a pesticide, wherein the adjuvant composition comprises:
        water;
        an organic acid;
        an organic amine;
        a mono-, di- or polysaccharide;
        an alkyl polyglycoside non-ionic surfactant; and
        an effective amount of a micronutrient consisting of zinc,
    wherein the pesticide comprises at least one salt capable of precipitating with the zinc,
    wherein the zinc is chelated with the organic acid and the organic amine, thereby preventing the zinc from precipitating with the pesticide,
    wherein a pH of the admixture is up to about 6.5, and
    wherein the agricultural admixture is adapted to increase uptake of zinc in seed, soil, foliage, or fruit.

2. The method of claim 1, wherein the pesticide comprises glyphosate.

3. The method of claim 2, further comprising admixing with hard water.

4. The method of claim 1, wherein the adjuvant composition and the pesticide are free of other micronutrients.

5. The method of claim 1, wherein the zinc is present at about 1 to about 10 wt % of the composition.

6. The method of claim 1, wherein the adjuvant is buffered to retain the pH of the admixture below about 6.5.

7. A method of improving uptake of zinc in seed, soil, foliar and fruit applications, the method comprising:
    applying to seed, soil, foliage or fruit, an adjuvant composition comprising:
        an organic acid;
        an organic amine;
        a mono-, di- or polysaccharide;
        an alkyl polysaccharide; and
        an effective amount of a micronutrient consisting of zinc,
    wherein the seed, soil, foliage or fruit increases uptake of the zinc.

8. The method of claim 7, wherein a pH of the applied adjuvant composition is up to about 6.5.

9. The method of claim 8, wherein the method further comprises admixing the adjuvant composition with a pesticide prior to foliar application.

10. The method of claim 9, wherein the pesticide comprises glyphosate.

11. The method of claim 10, wherein the adjuvant composition and the pesticide are free of other micronutrients.

12. The method of claim 11, wherein the zinc is present in the composition as zinc oxide at about 1 to about 10 wt % of the composition.

13. The method of claim 7, wherein the mono-, di- or polysaccharide comprises fructose.

14. The composition of claim 1, wherein the admixture is a solution.

* * * * *